United States Patent
Doherty

(10) Patent No.: US 8,362,056 B2
(45) Date of Patent: Jan. 29, 2013

(54) 4-HETEROARYL-SUBSTITUTED PHENOXYPHENYLACETIC ACID DERIVATIVES

(75) Inventor: George A. Doherty, Libertyville, IL (US)

(73) Assignee: Array BioPharma Inc., Boulder, CO (US)

( * ) Notice: Subject to any disclaimer, the term of this patent is extended or adjusted under 35 U.S.C. 154(b) by 378 days.

(21) Appl. No.: 12/739,560

(22) PCT Filed: Nov. 4, 2008

(86) PCT No.: PCT/US2008/082350
§ 371 (c)(1), (2), (4) Date: Jul. 13, 2010

(87) PCT Pub. No.: WO2009/061730
PCT Pub. Date: May 14, 2009

(65) Prior Publication Data
US 2010/0273850 A1  Oct. 28, 2010

Related U.S. Application Data

(60) Provisional application No. 60/985,463, filed on Nov. 5, 2007.

(51) Int. Cl.
| | |
|---|---|
| A01N 43/52 | (2006.01) |
| A01N 43/56 | (2006.01) |
| A01N 43/38 | (2006.01) |
| A61K 31/415 | (2006.01) |
| A61K 31/405 | (2006.01) |
| C07D 235/00 | (2006.01) |
| C07D 231/56 | (2006.01) |
| C07D 209/04 | (2006.01) |

(52) U.S. Cl. ..... 514/394; 514/403; 514/415; 548/304.4; 548/361.1; 548/469

(58) Field of Classification Search ........... 514/394, 514/403, 415; 548/304.4, 361.1, 469
See application file for complete search history.

(56) References Cited

FOREIGN PATENT DOCUMENTS

| WO | 2005044260 A1 | 5/2005 |
|---|---|---|
| WO | 2006092579 A1 | 9/2006 |
| WO | 2007019675 A1 | 2/2007 |
| WO | WO 2008024746 A1 * | 2/2008 |

OTHER PUBLICATIONS

Norman, Peter, Idole-based CRTH2 antagonist,, Expert Opinion Ther. Patents, vol. 15(12), (2005), pp. 1817-1823.
Pettipher, Roy, Antagonism of the prostaglandin D2 receptors DP1 and CRTH2 as an approach to treat allergic diseases, Drug Discovery, vol. 6, Apr. 2007, pp. 313-325.

* cited by examiner

*Primary Examiner* — Sreeni Padmanabhan
*Assistant Examiner* — Sarah Pihonaki
(74) *Attorney, Agent, or Firm* — John R. Moore, Esq.; Sarah M. Mastous; Viksnins Harris & Padys PLLP

(57) ABSTRACT

Compounds of Formula I: I in which $D^1$, $D^2$, $R^1$, $R^2$, $R^7$, $R^8$ and A have the meanings given in the specification, are DP2 receptor modulators useful in the treatment of immunologic diseases.

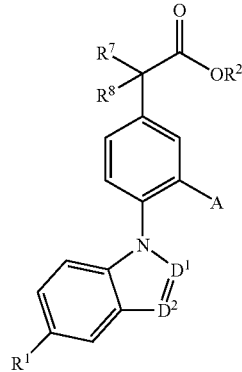

I

18 Claims, No Drawings

4-HETEROARYL-SUBSTITUTED PHENOXYPHENYLACETIC ACID DERIVATIVES

This application claims the benefit of U.S. provisional patent application number 60/985,463, filed Nov. 5, 2007, which is incorporated herein in its entirety.

The present invention relates to novel compounds, to pharmaceutical compositions comprising the compounds, to a process for making the compounds and to the use of the compounds in therapy. More particularly, it relates to certain 4-heteroaryl-sustituted phenoxyphenylacetic acid derivatives useful in the treatment and prevention of allergic disease such as asthma, allergic rhinitis and atopic dermatitis and other inflammatory diseases mediated by prostaglandin $D_2$ ($PGD_2$).

DP2 is a G-protein coupled receptor that is selectively expressed on cell types that mediate allergic inflammation including mast cells, basophils, eosinophils and Th2 cells and there is growing evidence that it plays a critical role in the pathophysiology of allergy (Hirai et. al., Journal of Experimental Medicine (2001) 193:255-261). The endogenous ligands for DP2 ($PGD_2$ and its active metabolites) are made by activated mast ceils and by Th2 cells, and can be readily detected at sites of allergic disease. Agonism of DP2 promotes the migration and or activation of basophils, eosinophils and Th2 cells in vitro and in vivo (Kostenis and Ulven, Trends in Molecular Medicine (2006) 12;1471-148-158), suggesting that this receptor may drive disease processes in vivo. In support of this mice made deficient in DP2 by gene inactivation through homologous recombination show evidence of reduced allergic responses so pre-clinical models of asthma and atopic dermatitis. Similar results have been reported using selective small molecule inhibitors of DP2 (reviewed in Pettipher, et. al., Nature Reviews Drug Discovery (2007) 6:313-325).

Clinical validation for DP2 as a target for allergic disease is also provided by Ramatroban (BAY u34505). Ramatroban was originally developed as a Thromboxane A2 (TP) receptor antagonist but showed unexpected clinical activity in allergy, which could not be readily explained by its activity against TP. It has recently been shown that Ramatroban is also an inhibitor of DP2 and its activity in pre-clinical models of allergy can be recapitulated using selective inhibitors of DP2 but not of TP (Sugimoto et. al. Journal of Pharmacology and Experimental Therapeutics (2003 ) 305:347-352; Takeshiti et. al., International Immunology (2004) 16:947-959). These findings support the view that the clinical efficacy seen with Ramatroban in allergic disease is due to its activity against DP2. Ramatroban is currently approved in Japan for the treatment of seasonal allergic rhinitis. Based on the validation of DP2 as a drug target in allergy many companies have sought to develop inhibitors of DP2 for the treatment of allergic disease, and the first of these have now entered clinical development.

International patent application publication number WO 2004/058164 discloses, inter alia, certain 2-substituted phenoxyphenylacetic acid derivatives that modulate the $PGD_2$-selective receptor CRTH2 (chemoattractant receptor-homologous molecule expressed on Th2 cells), now more commonly referred to as DP2. The compounds are said to be useful in the treatment of immunologic diseases such as asthma and allergic inflammation.

It has now been found that certain 4-heteroaryl-substituted phenoxyphenyl acetic acid derivatives bearing a particular substituent meta to the acetic acid moiety are DP2 receptor modulators. As used herein, the term "modulator" includes antagonists.

According to one aspect, the present invention provides a compound of general Formula I:

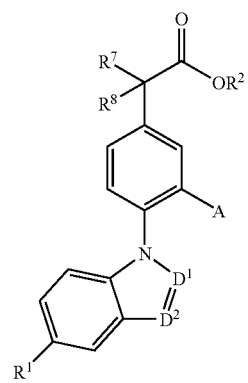

or a salt thereof, wherein:
$D^1$ is N or $CR^9$ and $D^2$ is N or $CR^{10}$, wherein at least one of $D^1$ and $D^2$ is not N;
$R^1$ is $Ar^1$-$L^1$-W-$L^2$-;
$L^2$ is —$(CR^6R^d)_m$—;
W is —$CONR^{3a}$—$NR^{3b}CO$— or —$SO_2NR^{3c}$—;
$R^{3a}$, $R^{3b}$ and $R^{3c}$ are each H or methyl;
$L^1$ is —$(CR^3R^b)_n$— or —$(CR^3R^b)O$—;
n and m are independently 0, 1 or 2;
each $R^a$, $R^b$, $R^c$ and $R^d$ is independently H, F, methyl or cyclopropyl,
or $R^a$ and $R^b$ or $R^c$ and $R^d$ together with the carbon to which they are attached form a cyclopropyl ring;
$Ar^1$ is phenyl, napthyl, or 2,3-dihydro-1H-indenyl each of which is unsubstituted or substituted with one or more groups independently selected front F, Cl, CN, $CF_3$, $CHF_2$, $CH_2F$, $SF_5$, methyl, ethyl and cyclopropyl provided that when $Ar^1$ is naphthyl or 2,3-dihydro-1H-indenyl then n is 0;
$R^2$ is H or $C_1$-$C_6$ alkyl;
A is CN, $CH_2NH_2$, $CH_2NR^{4a}C(=O)R^3$, $CH_2NR^{4b}SO_2R^6$ or Cl;
$R^{4a}$ and $R^{4b}$ are each H or methyl;
$R^5$ is $C_1$-$C_6$ alkyl, $C_1$-$C_6$ alkoxy, or $C_3$-$C_6$ cycloalkyl;
$R^6$ is $C_1$-$C_6$ alkyl, NH($C_1$-$C_6$ alkyl), or N($C_1$-$C_6$ alkyl)$_2$;
$R^7$ and $R^8$ are independently H or methyl; and
$R^9$ and $R^{10}$ are independently H, methyl, ethyl, isopropyl, $CF_3$, or cyclopropyl.

Compounds according to the present invention have been found to be DP2 modulators and are useful in the treatment of immunologic diseases such as asthma and allergic inflammation.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The term "halogen" as used herein includes F, Cl, Br, and I.

The term "$C_1$-$C_6$ alkyl" as used herein refers to a saturated linear or branched-chain monovalent hydrocarbon radical of one to six carbon atoms, respectively. Examples of alkyl groups include but are not limited to, methyl, ethyl, 1-propyl, 2-propyl, 1-butyl, 2-methyl-1-propyl, 3-butyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl,-2-pentyl, 4-methyl-2-pentyl, 3-methyl-3-pentyl, 2-methyl-3-pentyl, 2,3-dimethyl-2-butyl, and 3,3-dimethyl-2butyl.

The term "$C_1$-$C_6$ alkoxy" as used herein refers to a ($C_1$-$C_6$)—O— group, i.e., an alkyl group of 1-6 carbons of straight or branched attached to the parent structure through an oxygen atom. Exemplary alkoxy groups include methoxy, ethoxy, propoxy, isopropoxy, butoxy, t-butoxy, and isobutoxy.

In one embodiment, $D^1$ is $CR^9$ and $D^2$ is $CR^{10}$. In certain embodiments, $R^9$ are $R^{10}$ are both hydrogen.

In one embodiment $D^1$ is N and $D^2$ is $CR^{10}$. In certain embodiments, $R^{10}$ is hydrogen. In certain embodiments, $R^{10}$ is methyl.

In one embodiment $D^1$ is $CR^9$ and $D^2$ is N. In certain embodiments, $R^9$ is hydrogen. In certain embodiments, $R^9$ is methyl.

In one embodiment, W is —$CONR^{3a}$—. An example of a particular value for $R^{3a}$ is hydrogen. In one embodiment, W is —$NR^{3b}CO$—. In one embodiment, $R^{3b}$ is hydrogen. In another embodiment, $R^{3b}$ is methyl. Examples of particular values for W are CONH, NHCO and N(CH$_3$)CO.

In one embodiment, W is —$SO_2NR^{3a}$—. An example of a particular value for $R^{3a}$ is hydrogen.

In one embodiment, $L^1$ is —$(CR^aR^b)_a$—. Examples of particular values for n are 0, 1 and 2. In certain embodiments, $R^a$ is H and $R^b$ is H or methyl. In certain embodiments, $R^a$ and $R^b$ together with the carbon atom to which they are attached form a cyclopropyl ring. Examples of particular values for $L^1$ are a bond, —CH$_2$—, —CH$_2$CH$_2$—, cyclopropylideneCH$_2$—, —CH$_2$CH(CH$_3$)— and —CH$_2$C(CH$_3$)$_2$—.

In one embodiment, $L^1$ is —$(CR^aR^b)O$—. Exemplary embodiments include —CH$_2$—O— and —CH(CH$_3$)—O—.

Referring to $L^2$, examples of particular values for m are 0 and 1. Examples of particular values for $L^2$ are a bond and —CH$_2$—.

In certain embodiments, the sum of m and n is 0, 1 and 2. Particular mention is made of compounds in which the sum of m and n is 0, or 2.

Examples of values for -$L^1$-W-$L^2$- are —CONH—, —CH$_2$CONH—, —CH$_2$CH$_2$CONH—, —CONHCH$_2$—, —CH$_2$CONHCH$_2$—, —NHCO—, —CH$_2$NHCO—, —NHCOCH$_2$—, —CH$_2$CH$_2$NHCO—, —CH$_2$NHCOCH$_2$—, —CH$_2$CH$_2$NHCOCH$_2$—, —CH$_2$N(CH$_3$)COCH$_2$—, cyclopropylideneCH$_2$NHCO—, —CH$_2$ONHCO—, —SO$_2$NH—, —CH$_2$CH(CH$_3$)NHCO—, —CH$_2$C(CH$_3$)$_2$NHCO— and —CH(CH$_3$)ONHCO—.

Particular mention is made of compounds in which -$L^1$-W-$L^2$-is CH$_2$CH$_2$NHCO—, —CONH—, —CH$_2$CH(CH$_3$)NHCO—, CH$_2$C(CH$_3$)$_2$NHCO—, —NHCO—, —CH$_2$ONHCO— or —SO$_2$NH—.

In one embodiment, $Ar^1$ is a naphthyl group or a phenyl group, each of which is unsubstituted or substituted by one or two substituents selected independently from F, Cl and CF$_3$.

In one embodiment $Ar^1$ is 2,3-dihydro-1H-indenyl.

Examples of particular values for $Ar^1$ are naphthyl, phenyl, 4-fluorophenyl, 3,4-difluorophenyl, 2-chlorophenyl, 3-chlorophenyl, 4-chlorophenyl, 3,4-dichlorophenyl, 4-chloro-3fluorophenyl, 3-chloro-4fluorophenyl, 4-trifluoromethylphenyl 3-fluoro-4-trifluoromethylphenyl, 2,4-dichlorophenyl and 2,3-dihydro-1H-inden-2yl.

In one embodiment, A is CN.

In one embodiment, A is Cl.

In embodiment, A is CH$_2$NR$^{4a}$C(=O)R$^5$. An example of a particular value for $R^{4a}$ is hydrogen. In one embodiment, $R^5$ is $C_1$-$C_6$ alkyl, $C_1$-$C_6$ alkoxy or $C_3$-$C_6$ cycloalkyl. Examples of particular values for $R^3$ are methyl, methoxy, and cyclohexyl.

In one embodiment, A is CH$_2$NR$^{4b}$SO$_2$R$^6$. An example of a particular value for $R^{4b}$ is hydrogen. In one embodiment, $R^6$ is $C_1$-$C_6$ alkyl, NH)$C_1$- $C_6$ alkyl) or N($C_1$-$C_6$ alkyl)$_2$. Examples of values for $R^6$ are methyl and dimethylamino. A particular value for $R^6$ is $C_1$-$C_6$ alkyl, for example methyl.

A particular value for A when represented by CH$_2$NR$^{4b}$SO$_2$R$^6$ is CH$_2$NHSO$_2$CH$_3$.

In one embodiment, $R^2$ is hydrogen.

In one embodiment, $R^2$ is a $C_1$-$C_6$ alkyl group such as methyl, ethyl, propyl, isopropyl or t-butyl.

In one embodiment, both $R^7$ and $R^8$ are H. In certain embodiments $R^7$ is H and $R^8$ is methyl. In other embodiments, each of $R^7$ and $R^8$ is methyl.

According to another aspect, the present invention provides a process for the preparation a compound of Formula I or a salt thereof as defined hereinabove, which comprises:

(a) for a compound of Formula I in which A is CN, reacting a corresponding compound having the formula:

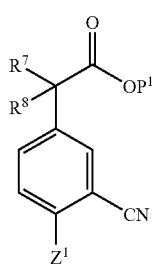

(II)

in which $R^7$ and $R^8$ are as defined herein, $P^1$ represents a hydrogen atom or a carboxyl protecting group, and $Z^1$ represents a leaving atom or group, with a compound having the formula

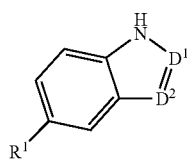

(III)

wherein $D^1$, $D^2$ and $R^1$ are as defined herein in the presence of a base; or (b) for a compound of Formula I in which A is —CH$_2$NH$_2$, reducing a corresponding compound formula (IV)

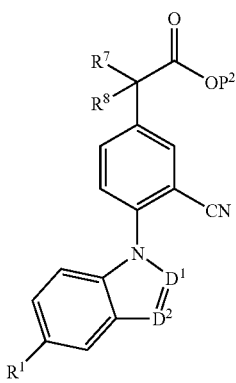

(IV)

in which $D^1$, $D^2$, $R^1$, $R^7$ and $R^8$ are as defined herein and $P^2$ is as defined for $P^1$; or (c) for a compound of Formula I in which A is $CH_2NR^{4a}C(=O)R^5$ or $CH_2NR^{4b}SO_2R^6$, reacting a corresponding compound of formula (VI)

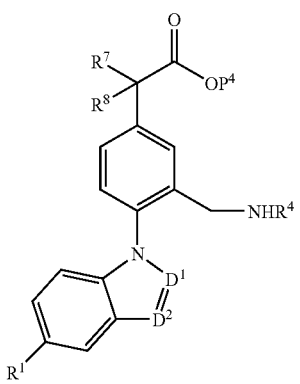

(VI)

in which $D^1$, $D^2$, $R^1$, $R^7$ and $R^8$ are as defined herein, $R^4$ is as defined for $R^{4a}$ and $R^{4b}$, and $P^4$ is as defined for $P^1$, with a compound of formula $R^3COZ^2$ or $R^6SO_2Z^3$ in which $Z^2$ and $Z^3$ each represents a leaving atom or group and $R^5$ and $R^6$ are as defined herein; or (d) coupling a corresponding compound of formula (VII)

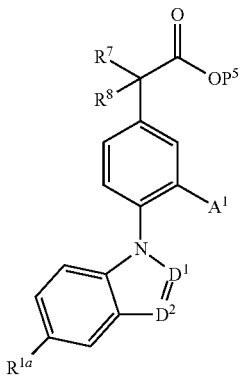

(VII)

in which $D^1$, $D^2$, $R^7$ and $R^8$ are as defined herein, $P^5$ is as defined for $P^1$, $A^1$ represents A or a protected form thereof and $R^{1a}$ represents H—$X^a$-$L^2$-in which $X^a$ represents HN, OC(=O) or $SO_2$, or a reactive derivative thereof, and $L^2$ is as defined herein, with a compound of formula (VIII)

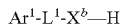

Ar$^1$-L$^1$-X$^b$—H (VIII)

in which $X^b$ represents C(=O)O or NH, or a reactive derivative thereof, and Ar$^1$ and L$^1$ are as defined herein; or (e) for a compound of formula I in which A is Cl or CN, coupling a corresponding compound having the formula (IX)

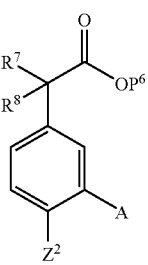

(IX)

in which $R^7$ and $R^8$ are as defined herein, $P^8$ is as defined for $P^1$, and 2 represents a leaving atom or group, with a compound having the formula (X)

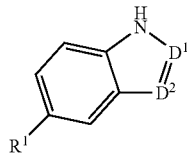

(X)

wherein $D^1$, $D^2$ and $R^1$ are as defined herein, in the presence of an appropriate metal catalyst and base; or (f) for a compound of formula (I) in which A is Cl, and $R^7$ and $R^8$ are each hydrogen, reacting a corresponding compound having the formula (XI):

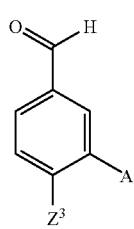

(XI)

in which $Z^1$ represents a leaving atom or group, with a compound having the formula

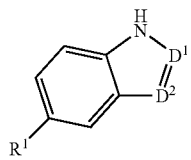

(III)

wherein $D^1$, $D^2$ and $R^1$ are as defined herein, in the presence of a base followed by homologation of the intermediate aldehyde (XII)

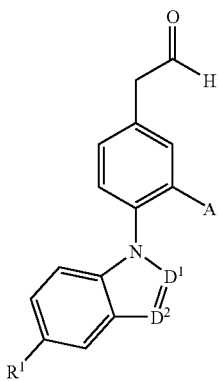

(XII)

to the corresponding carboxylic acid; and removing any protecting group or groups and, if desired, forming a salt.

Referring to process (a), the leaving atom or group represented by $Z^1$ may be, for example, a halogen atom such as a fluorine atom. The carboxyl protecting group may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. The base may be, for example, an alkali metal hydride or carbonate, such as sodium hydride, sodium carbonate or potassium carbonate, or a tertiary amine, such as triethylamine or N,N-diisopropylethylamine. Convenient solvents include amides, sulfoxides and nitriles, such as DMF, DMSO or acetonitrile. The reaction can be performed at an elevated temperature, such as in the range of from 50 to 150° C., as another example in the range of 120 to 130° C.

Compounds of formula (II) are known or can be prepared from the corresponding 3-halo compound, such as a corresponding 3-bromo compound, by treatment with CuCN.

Compound of formula (III) are known or can be prepared from treating a compound having the formula (XIII):

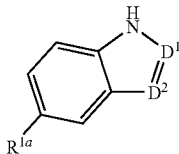

(XIII)

wherein $R^{1a}$ represents H—$X^8$-$L^2$-in which $X^8$ represents HN, OC(=O) or $SO_2$, or a reactive derivative thereof, and $L^2$ is as defined herein, with a compound of formula (VIII)

$Ar^1$-$L^1$-$X^b$—H  (VIII)

in which $X^b$ represents C(=O)O or NH, or a reactive derivative thereof, and $Ar^1$ and $L^1$ are as defined herein, Referring to process (b), the compound of formula (IV) can be reduced by hydrogenation in the presence of a Group VIII metal catalyst, such as Raney Ni with methanol/ammonia. The reaction can be conducted at a temperature in the range of from 0 to 100° C.

Referring to process (c) the leaving atom or group represented by $Z^2$ and $Z^3$ may be, for example, a halogen atom such as a fluorine atom or a leaving group sack as triflate. The reaction can be performed in the presence of a base, for example a tertiary amine such as diisopropyethylamine or pyridine. Convenient solvents include halogenated hydrocarbons, such as methylene chloride. The reaction can be conducted at a temperature in the range of from 0 to 100° C.

Referring to process (d), the coupling of the compound of formula (VII) with a compound of formula (VIII) may be performed using conventional amide bond formation conditions, for example by reacting an amine with a reactive derivative of a carboxylic acid, for example an acid halide, such as an acid chloride. An example of $A^1$ when it represents a protected form of A is a group of formula —$CH_2NR^4P^6$ in which $P^6$ represents an amine protecting group. The amine protecting group may be any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC).

Referring to process (e), the leaving atom represented by $Z^2$ may be, for example, a halogen atom such as a bromine or iodine atom. Alternatively, $Z^2$ may be a leaving group, such as an arylsulfonate, for example an aryltriflate. The coupling of compounds of the formula (IX) with a compound of the formula (X) occurs in the presence of a metal catalyst such as copper (I) iodide, a diamine co-catalyst and a base such as potassium phosphate in a suitable solvent such as toluene.

A compound of the formula (IX) where A is chloro and $Z^1$ is bromo can be prepared from 4-bromo-3-chlorobenzoic acid, which can be converted to its corresponding aldehyde and homologated as described in process (f).

A compound of the formula (IX) where A is cyano and $Z^1$ is bromo can be prepared from 2-bromo-5-iodobenzoic acid by conversion of the corresponding compound wherein A is a carboxylic acid group into the corresponding compound where A is a nitrile group, followed by selective replacement of the iodide with an allyl group using procedures described by Knochel (*Angew. Chem. Int. Ed.* 1998, 37, 1701-1703). Oxidative cleavage of the olefin to the carboxylic acid and installation of the appropriate protecting group provides the compound of Formula (IX) where A is cyano and $Z^1$ is bromo.

Referring to process (f), the leaving atom represented by $Z^1$ may be, for example, a halogen atom such as a fluorine atom. Alternatively, $Z^1$ may be a leaving group such as a triflate. The base may be, for example, an alkali metal hydride or carbonate, such s sodium hydride, sodium carbonate or potassium carbonate, or a tertiary amine, such as triethylamine or N,N-diisopropylethylamine. Convenient solvents include amides, sulfoxides or nitriles, such as DMF, DMSO or acetonitrile. The reaction can be performed at an elevated temperature, such as in the range of from 50 to 110° C., as another example in the range of 70-80° C. Homologation of the aldehyde (XII) to the carboxylic ester occurs upon treatment of compounds of formula (XII) with methyl (methylthio)methyl sufoxide and an appropriate base such as Triton-B in a solvent such as THF at elevated temperatures followed by treatment with HCl/ethanol.

A compound of the formula (XI) wherein A is chloro and $Z^3$ is bromo can be prepared from 4-bromo-3-chlorobenzoic acid, which can be converted to its corresponding aldehyde using routine procedures known to persons skilled in the art.

The ability of test compounds to act as DP2 inhibitors may be demonstrated by the assay described in Example A.

Compounds which are DP2 inhibitors are useful in the treatment of diseases or disorders mediated by $PGD_2$, for example, diseases or disorders associated with overproduction or dysregulation of $PGD_2$.

As used herein, the term treatment includes prophylaxis as well as treatment of an existing condition.

Examples of disorders or diseases that may be treated with compounds according to the invention include immunologic diseases.

Examples of immunologic diseases include allergic inflammatory diseases, such as asthma, atopic dermatitis allergic rhinitis, seasonal allergies, food allergies, contact hypersensitivity (e.g., nickel sensitivity), hyper-eosinophilic syndromes, and allergic conjunctivitis.

Additional diseases or disorders which may be treated with the compounds of this invention include inflammatory bowel diseases such as Crohn's disease, ulcerative, colitis, ileitis and enteritis, vasculitis, Behcet's syndrome, psoriasis and inflammatory dermatoses such s dermatitis, eczema, urticaria, viral cutaneous pathologies such as those derived from human papillomavirus, HIV or RLV infection, bacterial, fungal and other parasital cutaneous pathologies, and cutaneous lupus erythematosus, respiratory allergic diseases such as persensitivity lung diseases, chronic obstructive pulmonary disease and the like, autoimmune diseases, such as arthritis (including rheumatoid and psoriatic), systemic lupus erythematosus, type 1 diabetes, myasthenia gravis, multiple sclerosis, Graves' disease, glomerulonephritis and the like, graft rejection (including allograft rejection and graft-v-host disease), e.g., skin graft rejection, solid organ transplant rejection, bone marrow transplant rejection, fever, cardiovascular disorders such as acute heart failure, hypotension, hypertension, angina pectoris, mycardial infarction, cardiomyopathy, congestive heart failure, atherosclerosis, coronary artery disease, restenosis, thrombosis and vascular stenosis, cerebrovascular disorders such as traumatic brain injury, stroke, ischemic reperfusion injury and aneurysm, cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, fibrosis, connective tissue disease and sarcoidosis, genital and reproductive conditions such as erectile dysfunction, gastrointestinal disorders such as gastritis, ulcers, nausea, pancreatitis and vomiting; neurologic disorders, such as Alzheimer's disease, sleep disorders such as insomnia, narcolepsy, sleep apnea syndrome and Pickwick Syndrome, pain, renal disorders such as HIV, and bacterial infections such as sepsis, inflammation, flushing, nasal congestion, and otitis media.

Accordingly, another aspect of this invention provides a method or treating diseases or medical conditions in a mammal mediated by PGD2, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by $PGD_2$, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional drugs, for example an anti-inflammatory compound that works by the same or by a different mechanism of action. Examples include anti-inflammatory compounds, steroids (e.g., dexamethasone, cortisone and fluticasone), NSAIDs (e.g., ibuprofen, indomethacin, and ketoprofen), anti-histamines, and anti-leukotrienes (e.g., Singulair®).

The compounds of the invention may be administered by any convenient route, e.g. into the gastrointestinal tract (e.g. rectally or orally), the nose, lungs, musculature or vasculature of transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a PGD2-mediated condition. For example, in one embodiment the present invention provides a compound of Formula I or a pharmaceutically acceptable salt thereof, for use in the treatment of immunologic diseases such as allergic inflammatory diseases, such as asthma, atopic dermatitis, allergic rhinitis, seasonal allergies, food allergies, contact hypersensitivity (e.g., nickel sensitivity), hyper-eosinophilic syndromes, and allergic conjunctivitis.

According to a further aspect, the present invention provides the use of a compound of Formula I or a pharmaceutically acceptable salt thereof, in the manufacture of a medicament to treat a $PGD_2$-mediated condition such as an immunologic disorder, as defined hereinabove.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge and were used without further purification unless otherwise indicated. Tetrahydrofuran (THF) dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$HNMR spectra were obtained as $CDCl_3$, $CD_3OD$, or $d_6$-DMSO solutions (reported in ppm), using tetramethylsilane (0.00 ppm) or residual solvent (CDCl$_3$: 7.25 ppm; CD$_3$OD: 3.31 ppm; d$_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dr (doublet of triplets). Coupling constants, when given, are reported in Hertz (Hz).

Example A

DP-2 Binding Inhibition Assay

The coding sequence of human DP2 was introduced into the human Leukemic cell line K562 by electroporation and stable clones expressing DP2 were obtained by limiting dilation followed by cell surface staining with a rat monoclonal antibody specific for human DP2. Membranes were prepared from one of these DP2 expressing clones and used to determine the ability of the compounds of the present invention to inhibit binding of prostaglandin D2 (PGD$_2$) to its receptor DP2 by the following procedure. Membranes (1.25 μg/well) were mixed with $^3$H-labeled PGD$_2$ and various concentrations of test compounds in 130 μL of binding buffer (50 mM Tris-HCl, pH 7.4, 40 mM MgCl$_2$, 0.1% bovine serum albumin, 0.1% NaN$_3$) in 96-well U-bottom polypropylene plates. After incubation for 60 minutes at ambient temperature, the assay was transferred to a filtration plate (#MAFB; Millipore Corporation, Bedford, Mass.), and washed three times with binding buffer. Radioactivity was measured by a scintillation counter (TopCount; PerkinElmer Life Sciences, Boston, Mass.). Nonspecific binding was determined by incubations in the presence of 1 μM unlabeled PGD$_2$ or 5 μM of a known DP2 antagonist. IC$_{50}$ values for inhibition of binding are determined for each compound tested from the inflexion point of a standard 4-parameter logistical curve fitted to the values obtained. The compounds described in the Examples had IC$_{50}$ values less than 3 micromolar. Certain compounds described in the Examples had IC$_{50}$ values less than 1 micromolar.

Example 1

2-(4-(5-(4Chlorophenylethylcarbamoyl)-1-H-indol-1-yl)-3-cyanophenyl)acetic Acid

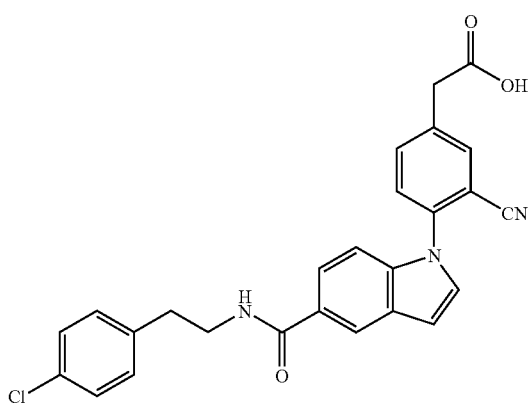 [SMILES: N#Cc1cc(CC(=O)O)ccc1-n1ccc2cc(C(=O)NCCc3ccc(Cl)cc3)ccc21]

Step A: 2-(3-Bromo-4-fluorophenyl)acetic acid (64 g, 275 mmol) was diluted with DMF (400 mL) followed by the addition of Cu(I)CN (49 g, 549 mmol). The reaction was heated to 130° C. and stirred for 12 hours. The reaction was allowed to cool and diluted with ethyl acetate and water, and the mixture was filtered. The organic layer was washed with water, 1N HCl, water and the brine. The organic layer was dried over MgSO$_4$, filtered and concentrated to yield 2-(3-cyano-4-fluorophenyl)acetic acid (36 g, 73% yield) as light yellow oil that solidified to a light yellow solid.

Step B: 2-(3-Cyano-4-fluorophenyl)acetic acid (14.3 g, 79.8 mmol) was diluted with THF (150 mL) followed by the addition of tert-butyl N,N'-diisopropylcarbamimidate (48.0 g, 239 mmol). After stirring for 12 hours, the reaction was filtered and the filtrate was concentrated. The residue was taken up in ethyl acetate 100 mL and washed with 1N HCl saturated bicarbonate water and brine. The organic layer was dried over MgSO$_4$, filtered and concentrated. Additional precipitate was removed by filtration. The remaining residue was purified on a Biotage 40M column eluting over silica gel with hexanes:ethyl acetate (9:1) to yield tert-butyl 2-(3-cyano-4-fluorophenyl)acetate (10.0 g, 53.3% yield) as a clear oil that later solidified to a white solid.

Step C: To a mixture of 2-(4-chlorophenyl)ethylamine (0.531 g, 3.41 mmol), indole-5-carboxylic acid (0.500 g, 3.10 mmol) and DIEA (0.811 mL, 4.65 mmol) in DCM (10 mL) was added HBTU (1.29 g, 3.41 mmol) and acetonitrile (5 mL), and the reaction was stirred at ambient temperature overnight. The reaction mixture was diluted with ethyl acetate (75 mL) and the organic layer was washed with 2N HCl (50 mL) and brine (50 mL), dried over magnesium sulfate and concentrated. The residue was purified by silica gel chromatography eluting with a gradient of 0.5% methanol/DCM to 10% methanl/DCM to provide N-(4chlorophenethyl)-1H-indole-5carboxamide (0.650 g, 70.1% yield) as waxy yellow solid.

Step D: To a mixture of tert-butyl 2-(3-cyano-4-fluorophenyl)acetate (0.150 g, 0.6376 mmol) and N-(4-chlorophenethyl)-1H-indole-5carboxamide (0.2095 g, 0.7014 mmol) in DMSO (3 mL) was added K$_2$CO$_3$ (0.1322 g, 0.9564 mmol), and the reaction mixture was heated at 120° C. for 30 minutes, then at 130° C. for 1 hour. The reaction was diluted with ethyl acetate and the organic layer was washed with water and brine, dried over magnesium sulfate and concentrated. The residue was purified by silica gel chromatography eluting with a gradient of 5% to 100% ethyl acetate/hexanes to provide tert-butyl 2-(4-(5-((4-chlorophenethyl)carbamoyl)-1H-indol-1-yl)-3cyanophenyl)acetate (0.160 g, 48.82% yield) as a waxy solid. MS (APCI)=514.0 (M+1).

Step E: To a solution of tert-butyl 2-(4-(5-((4-chlorophenethyl)carbamoyl)-1H-indol-1yl)-3cyanophenyl)acetate (0.043 g, 0.0837 mmol) in DCM (0.5 mL) was added TFA (0.50 mL, 6.49 mmol). The reaction mixture was stirred for 1 hour and then concentrated. The residue was purified by silica gel chromatography eluting with a gradient of 0.5% methanol/DCM with 0.5% AcOH to 5% methanol/DCM containing 0.5% AcOH to provide 2-(4-(5-((4-chlorophenethyl)carbamoyl)-1H-indol-1yl)-3-cyanophenyl)acetic acid as a white solid. $^1$H NMR (400 MHz, CD$_3$OD) δ 8.15 (s, 1H), 7.91 (s, 1H), 7.81 (d, J=7.7 Hz, 1H), 7.67 (d, J=8.6 Hz, 1H), 7.62 (d, J=8.4 Hz, 1H), 7.56 (d, J=3.0 Hz, 1H), 7.24-7.34 (m, 5H), 6.84 (d, J=3.9 Hz, 1H), 3.83 (s, 2H), 3.62 (t, J=7.5 Hz, 2H), 2.93 (t, J=7.4 Hz, 2H), MS(APCI)=458.1(M+1).

Example 2

2-(4-(5-(4-Chlorophenethylcarbamoyl)-1H-indol-1-yl)-3-(methylsulfonamidomethyl)phenyl)acetic Acid

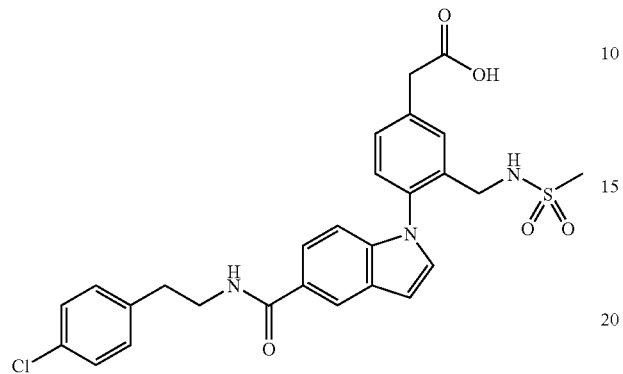

Step A: To a solution of tert-butyl 2-(4-(5-((4-chlorophenethyl)carbamoyl)-1H-indol-1yl)-3-cyanophenyl)acetate (Example 1, Step D; 0.160 g, 0.311 mmol) in 7N $NH_3$ in methanol (5 mL) was added Raney-Ni as a suspension in water and the reaction stirred under an atmosphere of hydrogen for 16 hours. The reaction was filtered and concentrated, and the residue was azeotroped with toluene to give tert-butyl 2-(4-(5-((4-chlorophenethyl)carbamoyl)-1H-indol-1-yl)-3-(aminomethyl)phenyl)acetic (0.075 g, 46.5% yield).

Step B: To a solution of tert-butyl 2-(4-(5-((4-chlorophenethyl)carbamoyl)-1H-indol-1yl)-3-(aminomethyl)phenyl)acetic (0.075 g, 0.1448 mmol) and DIEA (0.03783 mL, 0.2172 mmol) in methylene chloride (0.5 mL) was added methanesulfonyl chloride (0.01368 mL, 0.1737 mmol). After stirring for 1 hour, the reaction mixture was loaded onto a silica gel samplet and the product was eluted using a gradient of 0.5% methanol/DCM to 5% methanol/DCM. Isolated tert-butyl 2-(4-(5-((4-chlorophenethyl)carbamoyl)-1H-indol-1yl)-3-(methylsulfanamidomethyl)phenyl)acetic (0.056 g, 64.89% yield).

Step C: To a solution of tert-butyl 2-(4-(5-((4-chlorophenethyl)carbamoyl)-1H-indol-1yl)-3-(methylsulfanamidomethyl)phenyl)acetic (0.056 g, 0.094 mmol) in DCM (0.5 mL) was added trifluoroacetic acid (0.5 mL, 0.094 mmol). After stirring for 1 hour, the reaction mixture was concentrated and loaded onto a silica gel samplet with DCM. The product was eluted using a gradient of 0.5% methanol/DCM containing 0.5% AcOH to 10% methanol/DCM containing 0.5% AcOH. Isolated 2-(4-(5-((4-chlorophenethyl)carbamoyl)-1H-indol-1yl)-3-(methylsulfonamidomethyl)phenyl)acetic acid (0.036 g, 71% yield) as a white solid. $^1$H NMR (400 MHz, $CD_3OD$) δ 8.45 (t, J=5.9 Hz, NH), 8.14 (s, 1H), 7.67 (s, 1H), 7.60 (d, J=8.6 Hz, 1H), 7.43 (d, J=7.8 Hz, 1H), 7.41 (d, J=3.2 Hz, 1H), 7.21-7.35 (m, 5H), 7.05 (d, J=8.7 Hz, 1H), 6.79 (d, J=3.8 Hz, 1H), 3.94 (d, J=3.7 Hz, 2H), 3.77 (s, 2H), 3.61 (q, J=6.5 Hz, 2H), 2.93 (t, J=7.3 Hz, 2H), 1.99 (s, 3H). MS(APCI)=540.1 (M+1).

Example 3

2-(3Cyano-4-(5-(3,4-dichlorobenzamido)-1H-indol-1yl)phenyl)Acetic Acid

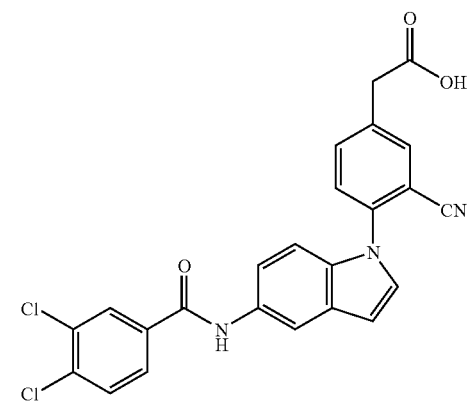 [SMILES: N#Cc1cc(CC(=O)O)ccc1-n1ccc2cc(NC(=O)c3ccc(Cl)c(Cl)c3)ccc21]

Step A: A mixture of tert-butyl 2-(3-cyano-4-fluorophenyl)acetate (0.600 g, 2.550 mmol) and 5-nitro-1H-indole (0.4549 g, 2.805 mmol) and $K_2CO_3$ (0.5287 g, 3.826 mmol) was heated in DMSO (7 mL) at 90° C. overnight. The reaction was cooled and then directly loaded onto a silica gal samplet, eluting with a gradient of 5% ethyl acetate/hexanes to 50% ethyl acetate/hexanes to provide tert-butyl 2-(3cyano-4-(5-nitro-1H-indol-1yl)phenyl)acetic (0.842 g, 87.48% yield) as a colorless oil.

Step B: To a solution of tert-butyl 2-(3cyano-4-(5-nitro-1H-indol-1yl)phenyl)acetic (0.842 g, 2.23 mmol) in THF (10 mL) was added Zn dust (0.5 g, 7.65 mmol) followed by the drop wise addition of aqueous ammonium chloride. The reaction mixture was diluted with ethyl acetate (100 mL), and the organic layer was washed with water and brine, dried over magnesium sulfate and concentrated to give tert-butyl 2-(4-(5-amino-1H-indol-1yl)phenyl)-3-cyanophenyl)acetic (0.710 g, 91.6% yield) as a yellow solid.

Step C: To a solution of tert-butyl 2-(4-(5-amino-1H-indol-1yl)-3-cyanophenyl)acetic (0.035 g, 0.10 mmol) and DIEA (0.026 mL, 0.15 mmol) in DCM (0.5 mL) was added 3,4-dichlorobenzoyl chloride (0.023 g, 0.11 mmol). After stirring for 15 minutes, the reaction was loaded onto silica gel, silica gel, eluting with a gradient of 5% ethyl acetate/hexanes to 40% ethyl acetate/hexanes to provide tert-butyl 2-(3-cyano-4-(5-(3,4-dichlorobenzamido)-1H-indol-1-yl)phenyl)acetate (0.042 g, 80% yield) as a white solid.

Step D: To a solution or tert-butyl 2-(3-cyano-4-(5-(3,4-dichlorobenzamido)-1H-indol-1-yl)phenyl)acetate (0.040 g, 0.769 mmol) in DCM was added TFA (0.50 mL, 6.49 mmol), and the reaction mixture was stirred for 1 hour at ambient temperature. The reaction was concentrated, and the residue was purified by silica gel chromatography, eluting with a gradient of 0.5% MeOH/DCM containing 0.5% AcOH to 5% MeOH/DCM containing 0.5% AcOH to provide 2-(3-cyano-4-(5-(3,4-dichlorobenzamido)-1H-indol-1-yl)phenyl)acetate acid as a white solid. $^1$H NMR (400 MHz, $CD_3OD$) δ 8.14 (s, 1H), 8.03 (s, 1H), 7.87-7.94 (m, 2H), 7.79 (d, J=8.0 Hz, 1H), 7.69 (d, J=8.5 Hz, 1H), 7.62 (d, J=8.6 Hz, 1H), 7.51(d, J=3.3 Hz, 1H), 7.45 (d, J=8.8 Hz, 1H), 7.30 (d, J=9.4 Hz, 1H), 6.75 (d, J=3.3 Hz, 1H), 3.81 (s, 2H). MS(APCI)=464.4 (M+1).

Example 4

2-(3Cyano-4-(5-(3,4-dichlorophenylsulfonamido)-1H-indol-1yl)phenyl)Acetic Acid

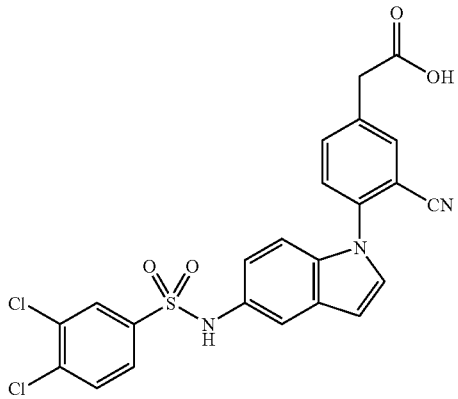 [SMILES: N#Cc1cc(CC(=O)O)ccc1-n1ccc2cc(NS(=O)(=O)c3ccc(Cl)c(Cl)c3)ccc21]

Step A: To a solution of tert-butyl 2-(3-cyano-4-(5-(3,4-dichlorobenzamido)-1H-indol-1-yl)phenyl)acetate (Example 3, Step B, 0.048 g, 0.14 mmol) and DIEA (0.036 mL, 0.21 mmol) in DCM (0.5 mL) was added 3,4-dichlorobenzene-1-sulfonyl chloride (0.037 % 0.15 mmol). After stirring for 30 minutes at ambient temperature, the reaction was loaded onto a silica gel column. The product was eluted using a gradient of 5% ethyl acetate/hexanes to 40% ethyl acetate/hexanes. Isolated tert-butyl 2-(3-cyano-4-(5-(3,4-dichlorobenzamido)-1H-indol-1-yl)phenyl)acetate (0.058 g, 75% yield) as a white solid.

Step B: To a solution of tert-butyl 2-(3-cyano-4-(5-(3,4-dichlorobenzamido)-1H-indol-1-yl)phenyl)acetate (0.058 g, 0.104 mmol) in DCM (0.5 mL) was added TFA (0.50 mL, 6.49 mmol). After stirring for 1 hour at ambient temperature, the reaction mixture was concentrated and loaded onto a silica gel column. The product was eluted using a gradient of 0.5% MeOH/DCM containing 0.5% AcOH to 5% MeOH/DCM containing 0.5% AcOH. Isolated 2-(3-cyano-4(5-(3,4-dichlorophenylsulfonamido)-1H-indol-1-yl)phenyl)acetic acid (0.032 g, 61.4% yield) as a white solid. MS(ESI)=500.1 (M+1).

Example 5

2-(3-Cyano-4-(5-(2,4-dichlorophenethylcarbamoyl)-1H-indol-1yl)phenyl)acetic Acid

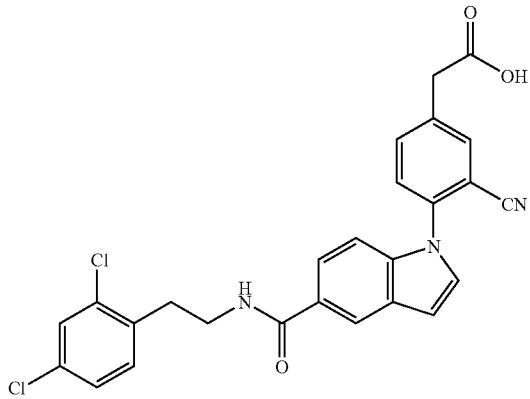

Step A: 2-(3-Cyano-4fluorophenyl)acetic acid (4.0 g, 22.3 mmol) was diluted with THF (10 mL) and methanol (2 mL), placed under nitrogen and cooled to 0° C. TMSCHN$_2$ (16.7 mL, 33.5 mmol) was added dropwise and the reaction was stirred for 30 minutes. The reaction was quenched with water and diluted with DCM. The layers were separated and the organic layer was dried over MgSO$_4$, filtered and concentrated. The residue was purified using a Biotage 40M cartridge eluting with hexanes ethyl acetate (9.1) to yield methyl 2(3-cyano-4-fluorophenyl)acetate (1.76 g, 9.11 mmol, 41%) as clear oil that solidified to a white solid. $^1$H NMR (400 MHz, CDCl$_3$) δ 7.48-7.59 (m, 2H), 7.19 (t, J=8.2 Hz, 1H), 3.73 (s, 3H), 3.64 (s, 2H).

Step B: Indole-5-carboxylic acid (1.00 g, 6.21 mmol) and tert-butyl N,N'-diisopropylcarbamimidate 2.29 g) were combined in 15 mL of THF and the reaction mixture was stirred for 25 hours. The reaction mixture was concentrated and the residue was purified on a silica gel column eluting with a gradient of 5% ethyl acetate/hexane to 100% ethyl acetate to provide tert-butyl 1H-indole-5-carboxylate (0.800 g, 3.68 mmol, 59%.)

Step C: tert-Butyl 1H-indole-5carboxylate (0.800 g, 3.68 mmol), methyl 2-(3-cyano-4-fluorophenyl)acetate (0.593 g, 3.07 mmol), and potassium carbonate (0.509 g, 3.68 mmol) were combined in 15 mL of DMSO and the reaction mixture was stirred at 95° C. for 24 hours. Reaction was diluted with ethyl acetate washed twice with water, dried over magnesium sulfate and concentrated. Silica gel chromatography eluting with a gradient of 5% ethyl acetate/hexanes to 60% ethyl acetate/hexanes gave tert-butyl 1-(2-cyano-4-(2-methoxy-2-oxoethyl)phenyl)-1H-indole-5-carboxylate (0.380 g, 0.973 mmol, 32%). MS (APCI)=390.9 (M+1).

Step D: tert-butyl 1-(2-cyano-4-(2-methoxy-2-oxoethyl)phenyl)-1H-indole-5-carboxylate (0.380 g, 0.973 mmol, in 2 ml of DCM was added 2 mL of TFA and the reaction stirred at ambient temperature under nitrogen. After 2 hours, the reaction was concentrated to give 1-(2-cyano-4-(2-methoxy-2-oxoethyl)phenyl)-1H-indole-5-carboxylic acid (0.320 g, 0.957 mmol, 98%). MS (APCI negative)=333.2 (M–1).

Step E: 1-(2-cyano-4-(2-methoxy-2-oxoethyl)phenyl)-1H-indole-5-carboxylic acid (0.020 g, 0.078 mmol, triethylamine (0.013 mL, 0.090 mmol) and oxalyl chloride (0.010 g, 0.079 mmol) was combined in 1 mL of DCM and 1 drop of DMF was added. The reaction mixture was stirred at ambient temperature for 30 minutes. To the reaction mixture was added 2-(2,4-dichlorophenyl)ethanamine.The reaction mixture was stirred for 1 hour then loaded onto a silica gel column. The product was eluted with solvent system of 5% EtOAc/Hexanes to 100% EtOAc to provide methyl 2-(4-(5-((2,4-dichlorophenethyl)carbamoyl)-1H-indol-1-yl)-3-cyanophenyl)acetate (0.170 g, 0.034 mmol). MS(APCI)=506.1 (M+1).

Step F: To a stirred solution of methyl 2-(4-(5-((2,4-dichlorophenethyl)carbamoyl)-1H-indol-1-yl)-3-cyanophenyl)acetate in methanol (1 mL) at ambient temperature was added aqueous sodium hydroxide (5.0 N, 0.036 mL) and 5 drops of water, and the reaction was stirred for 1 hour. The reaction mixture was taken up in DCM (5 mL) and washed with 2 M HCl (5 mL). The organic layer was dried over MgSO$_4$ and concentrated to give the desired compound as a white solid $^1$H NMR (400 MHz, CDCl$_3$) δ 8.08 (s, 1H), 7.80 (s, 1H), 7.70 (dd, J=8.5, 2.1 Hz, 1H), 7.65 (d, J=8.6Hz, 1H), 7.57 (d, J=8.9 Hz, 1H), 7.44 (d, J=5.9 Hz, 1H), 7.32 (d, J=8.7 Hz, 1H), 7.17-7.25 (m, 3H), 6.82 (d, J=3.0 Hz, 1H), 6.24 (d, J=5.9 NH), 3.81 (s, 2H), 3.74 (q, J=6.6 Hz, 2H), 3.10 (t, J=7.0 Hz, 2H), MS(ESI)=492.3 (M+1).

Example 6

2-(4-5-((1-(4Chlorophenyl)propan-2-yl)carbamoyl)-1H-indol-1-yl)-3cyanophenyl)acetic acid

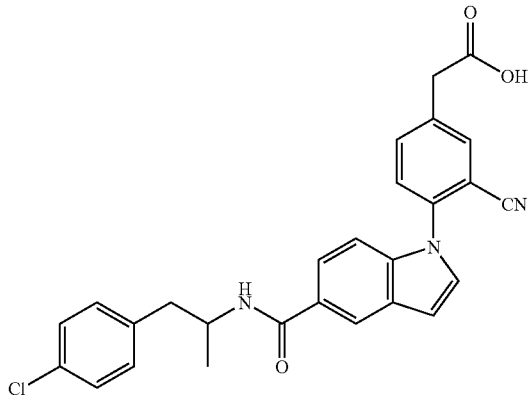

Prepared by the method of Example 5, substituting 2-(2,4-dichlorophenyl)ethanamine in Step E with 1-(4-chlorophenyl)propan-2-amine. ¹H NMR (400 MHz, CDCl₃) δ 8.04 (s, 1H), 7.80 (s, 1H), 7.69 (dd, J=1.5, 8.5, 1H), 7.63 (d, J=7.6Hz, 1H), 7.55 (d, J=7.6 Hz, 1H), 7.43 (d, J=3.1 Hz, 1H), 7.25-7.34 (m, 3H), 7.18 (d, J=8.5 Hz, 2H), 6.82 (d, J=3.0 Hz, 1H), 5.96 (d, J=8.0 Hz, 1H), 4.45-4.54 (m, 1H), 3.81 (s, 2H), 2.96 (dd, J=5.5 Hz, 13.1 Hz, 1H), 2.86 (dd, J=7.1 Hz, 13.2 Hz, 1H), 1.24 (d, J=6.8 Hz, 3H). MS(pos ESI)=472.2 (M+1).

Example 7

2-(4-5-((1-(4Chlorophenyl)-2methylpropan-2-yl)carbamoyl)-1H-indol-1-yl)-3-cyanophenyl)acetic acid

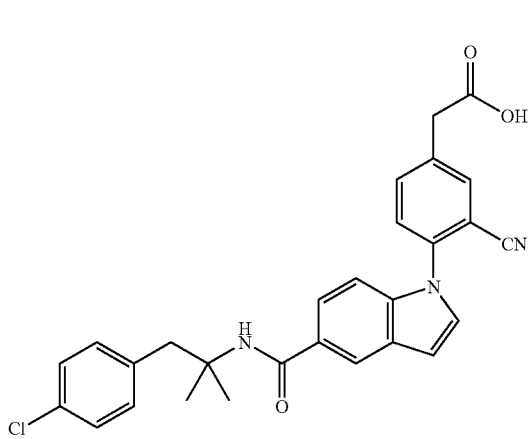 [SMILES: CC(C)(Cc1ccc(Cl)cc1)NC(=O)c1ccc2c(ccn2-c2ccc(CC(=O)O)cc2C#N)c1]

Prepared by the method of Example 5, substituting 2-(2,4-dichlorophenyl)ethanamine in Step E with 1-(4-chlorophenyl)-2-methylpropan-2-amine. ¹H NMR (400 MHz, CDCl₃) δ 8.01 (s, 1H), 7.80 (s, 1H), 7.70 (d, J=8.5 Hz, 1H), 7.55-7.62 (m, 2H), 7.43 (d, J=7.8 Hz, 1H), 7.31 (d, J=7.8 Hz, 1H), 7.22 (d, J=8.8 Hz, 2H), 7.12 (d, J=7.7 Hz, 2H), 6.81 (d, J=3.7 Hz, 1H). 5.73 (s, NH), 3.82 (s, 2H), 3.22 (s, 2H), 1.46 (s, 6H). MS(pos ESI)=486.2 (M+1).

Example 8

2-(3-Cyano-4-(5-(3,4-dichlorophenethylcarbamoyl)-1H-indol-1-yl)phenyl)acetic Acid

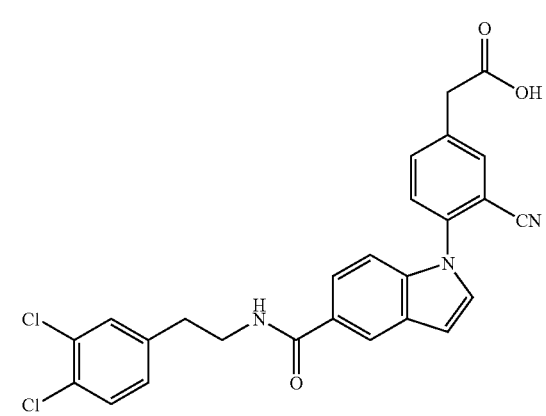 [SMILES: N#Cc1cc(CC(=O)O)ccc1-n1ccc2cc(C(=O)NCCc3ccc(Cl)c(Cl)c3)ccc21]

Prepared by the method of Example 5, substituting 2-(2,4-dichlorophenyl)ethanamine in Step E with 2-(3,4-dichlorophenyl)ethanamine. ¹H NMR (400 MHz, CDCl₃) δ 8.07 (s, 1H), 7.80 (s, 1H), 7.71 (d, J=7.8, 1H), 7.64 (d, J=8.6 Hz, 1H), 7.57 (d, J=8.7 Hz, 1H), 7.44 (d, J=4.0 Hz, 1H), 7.40 (s, 1H), 7.32 (d, J=8.6 Hz, 1H), 7.11 (d, J=8.6 Hz, 1H). 6.82 (d, J=3.0 Hz, 1H), 6.19 (t, J=5.6 Hz, NH), 3.81 (s, 2H), 3.73 (s, 2H), 3.73 (q, J=6.4Hz, 2H), 2.94 (t, J=7.0 Hz, 2H). MS(pos ESI) =492.2 (M+1).

Example 9

2-(3-Cyano-4-(5-(2,3-dihydro-1H-inden-2-ylcarbamoyl)-1H-indol-1-yl)phenyl)acetic Acid

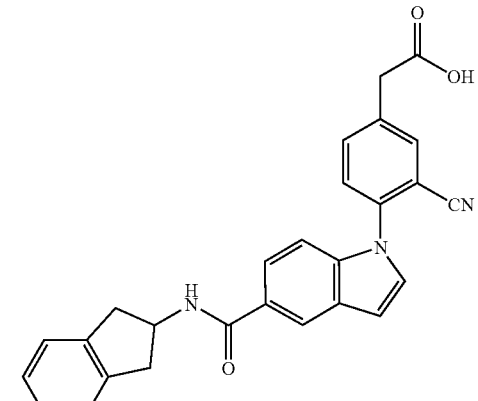

Prepared by the method of Example 5, substituting 2-(2,4-dichlorophenyl)ethanamine in Step E with 2,3-dihydro-1H-inden-2amine. ¹H NMR (400 MHz, CDCl₃) δ 8.07 (s, 1H), 7.79 (s, 1H), 7.67 (d, J=8.8 Hz, 2H), 7.54(d, J=8.7 Hz, 1H), 7.41 (d, J=3.9 Hz, 1H), 7.25-7.33 (m, 1H), 7.18-7.23 (m, 2H), 6.80 (d, J=3.2 Hz, 1H), 6.40 (d, J=7.7 Hz, NH), 4.95-5.07 (m, 1H), 3.80 (s, 2H), 3.46 (dd, J=7.1, 15.8 Hz, 2H) 2.95 (dd, J=5.0, 16.4 Hz, 2H). MS(pos ESI)=436.3 (M+1).

Example 10

2-(4-(5-Benzyloxycarbamoyl)-1H-indol-1-yl)-3-cyanophenyl)acetic Acid

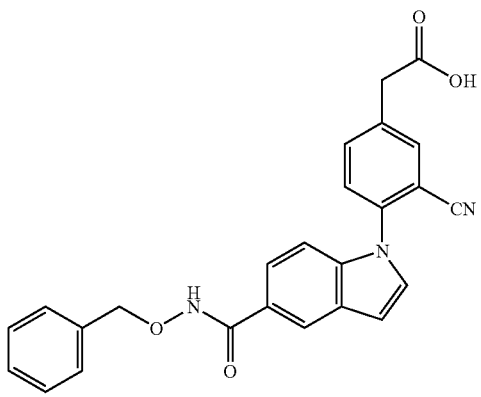 [SMILES: N#Cc1cc(CC(=O)O)ccc1-n1ccc2cc(C(=O)NOCc3ccccc3)ccc21]

Prepared by the method of Example 5, substituting 2-(2,4-dichlorophenyl)ethanamine in Step E with O-benzylhydroxylamine. $^1$H NMR (400 MHz, CDCl$_3$) δ 8.05 (s, 1H), 7.80 (s, 1H), 7.70 (dd, J=8.8, 1.9 Hz, 1H), 7.59 (d, J=7.42 Hz, 1H), 7.53 (d, J=8.1 Hz, 1H), 7.49 (d, J=5.2 Hz, 2H), 7.33-7.45 (m, 4H), 7.30 (d, J=8.5 Hz, 1H), 6.80 (d, J=3.5 Hz, 1H), 5.07 (s, 2H), 3.76 (s, 2H), MS(pos ESI)=448.0 (M+Na).

Example 11

2-(4-(5-((4-Chlorobenzyloxy)carbamoyl)-1H-indol-1-yl)-3-cyanophenyl)acetic Acid

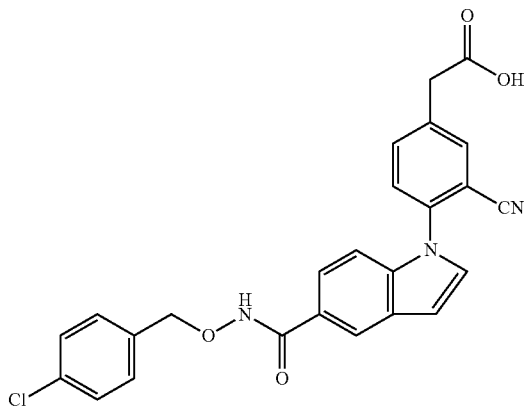 [SMILES: N#Cc1cc(CC(=O)O)ccc1-n1ccc2cc(C(=O)NOCc3ccc(Cl)cc3)ccc21]

Step A: A mixture of 1-(bromomethyl)-4-chlorobenzene (1.23 g, 6.01 mmol), tert-butyl hydroxycarbamate (1.00 g, 7.51 mmol), and potassium carbonate (1.25 g, 9.01 mmol) in 15 mL of acetonitrile was stirred at 80° C. for 4 hours. The reaction was cooled and 25 mL of DCM was added. The reaction mixture was washed with water and brine. The organic layer was dried over MgSO$_4$, filtered, and concentrated. The residue was purified on a silica gel column, eluting with a solvent system of 5% EtOAc/Hexanes to 60% EtOAC/Hexanes. Isolated tert-butyl 4-chlorobenzyloxycarbamate (1.28 g, 4.97 mmol).

Step B: A mixture of tert-butyl 4-chlorobenzyloxycarbamate (1.28 g, 4.97 mmol) in 15 mL of 4 M HCl-dioxane was stirred at ambient temperature for 1.5 hours. The reaction was concentrated to provide O-(4-chlorobenzyl)hydroxylamine (0.95 g, 4.90 mmol).

Step C: O-chlorobenzyl)hydroxylamine was reacted with 1-(2-cyano-4-(2-methoxy-2-oxoethyl)phenyl)-1H-indole-5-carboxylic acid in the presence of triethylamine and oxalyl chloride according to the method of Example 5, Step E, to provide 2-(4-(5-((4-chlorobenzyloxy)carbamoyl)-1H-indol-1-yl)-3-cyanophenyl)acetic acid. $^1$H NMR (400 MHz, CD$_3$OD) δ 8.10 (s, 1H), 7.91 (s, 1H), 7.80 (d, J=8.6 Hz, 1H), 7.56-7.64 (m, 3H), 7.50 (d, J=8.7 Hz, 2H), 7.41 (d, J=8.6 Hz, 2H), 7.33 (d, J=8.5 Hz, 1H), 6.85 (d, J=4.1 Hz, 1H), 4.98 (s, 2H), 3.81 (s, 2H).

Example 12

2-(3-Cyano-4-(5-(3,4-dichlorobenzyloxycarbamoyl)-1H-indol-1-yl)phenyl)acetic Acid

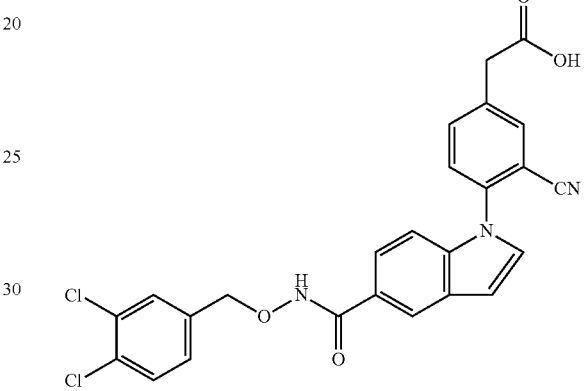

Prepared by the method of Example 5, substituting 2-(2,4-dichlorophenyl)ethanamine in Step E with O-(3,4-dichlorobenzyl)hydroxylamine. $^1$NMR (400 MHz, CD$_3$OD) δ 8.10 (s, 1H), 7.91 (s, 1H), 7.80 (d, J=1.6, 7.7 Hz, 1H), 7.71 (s, 1H), 7.53-7.64 (m, 4H), 7.43 (d, J=7.8 Hz, 1H), 7.33 (d, J=8.7 Hz, 1H), 6.85 (d, J=3.2 Hz, 1H), 4.98 (s, 2H), 3.82 (s, 2H).

Example 13

2-(3-Cyano-4-(5-(2,4-dichlorobenzyloxycarbamoyl)-1H-indol-1yl)phenyl)acetic Acid

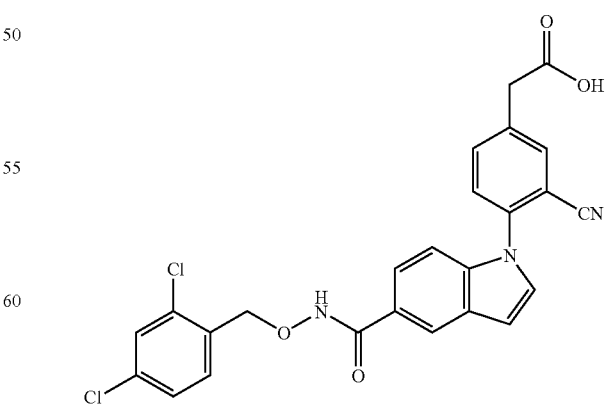

Prepared by the method of Example 11, substituting 1-(bromomethyl),-4-chlorobenzene in Step E with 4-(chlorophenyl)-1,2-dichlorobenzene. ¹H NMR (400 MHz, CD₃OD) δ 8.10 (s, 1H), 7.91 (s, 1H), 7.79 (d, J=7.8 Hz, 1H), 7.59-7.66 (m, 3H), 7.59 (d, J=3.9 Hz, 1H), 7.53 (s, 1H), 7.39 (d, J=6.3 Hz, 1H), 7.33 (d, J=8.7 Hz, 1H), 6.85 (d, J=3.2 Hz, 1H), 5.13 (s, 2H), 3.81 (s, 2H).

Example 14

2-(4-(5-(4-Chlorophenethylcarbamoyl)-1H-benzo[d]imidazol-1-yl)-3cyanophenyl)acetic Acid 1H), 7.35 (d, J=7.6 Hz, 2H), 7.29 (d, J=8.4 Hz, 2H), 3.85 (s, 2H), 3.48-3.56 (m, 2H), 2.88 (tm J=7.1 Hz, 2H), MS(APCI)= 459.2 (M+1).

Example 15

2-(4-(5-(4-Chlorophenethylcarbamoyl)-2methyl-1H-benzol[d]imidazol-1-yl)-3-cyanophenyl)acetic Acid and 2-(4-(6-(4-Chlorophenethylcarbamoyl)-2methyl-1H-benzol[d]imidazol-1-yl)-3-cyanophenyl)acetic Acid

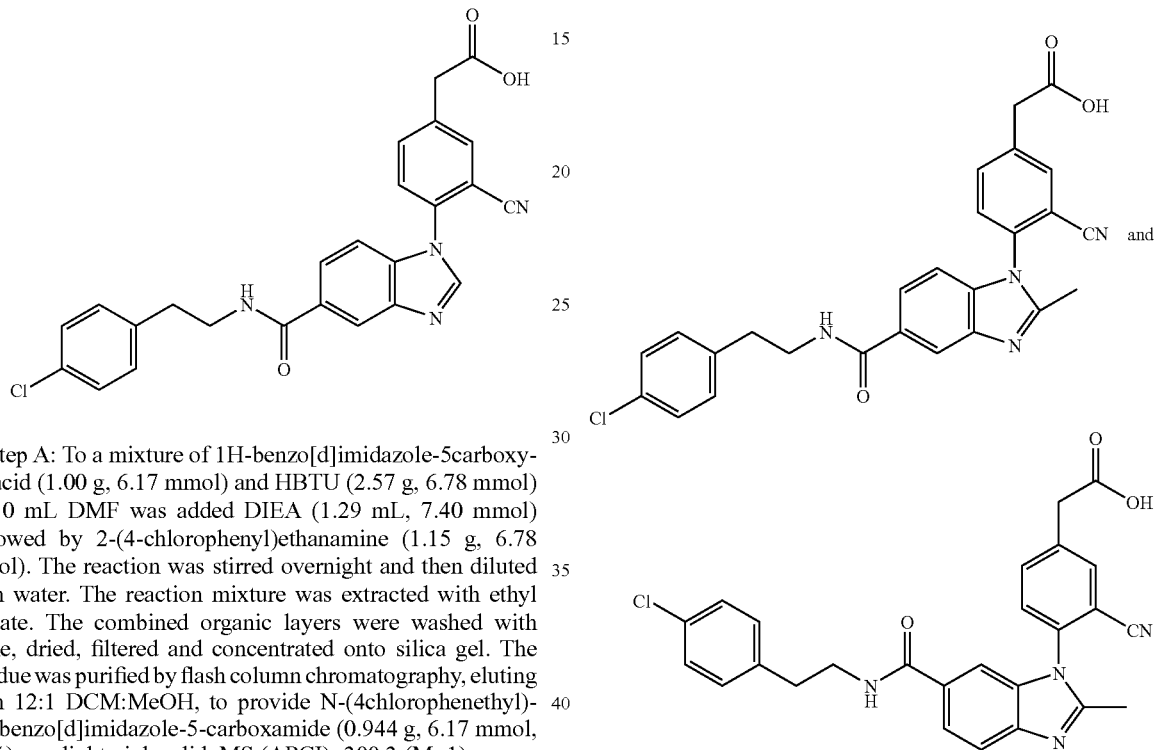

Step A: To a mixture of 1H-benzo[d]imidazole-5carboxylic acid (1.00 g, 6.17 mmol) and HBTU (2.57 g, 6.78 mmol) in 10 mL DMF was added DIEA (1.29 mL, 7.40 mmol) followed by 2-(4-chlorophenyl)ethanamine (1.15 g, 6.78 mmol). The reaction was stirred overnight and then diluted with water. The reaction mixture was extracted with ethyl acetate. The combined organic layers were washed with brine, dried, filtered and concentrated onto silica gel. The residue was purified by flash column chromatography, eluting with 12:1 DCM:MeOH, to provide N-(4chlorophenethyl)-1H-benzo[d]imidazole-5-carboxamide (0.944 g, 6.17 mmol, 51%) as a light pink solid. MS (APCI)=300.3 (M+1).

Step B: A mixture of tert-butyl 2-(3-cyano-4-fluorophenyl) acetate (0.250 g, 1.06 mmol), N-(4-chlorophenethyl)-1H-benzo[d]imidazole-5-carboxamide (0.54 g, 1.80 mmol) and potassium carbonate (0.18 g, 1.30mmol) in 5 mL DMSO was heated to 100° C. for 1 hour, then at ambient temperature overnight, and then at 100° C. for 6 hours. The reaction mixture was cooled to ambient temperature and poured into 2:1 water:saturated Na₂CO₃. The precipitate was collected by filtration. The residue was dissolved in ethyl acetate and purified by flash chromatography, eluting with 5:1 hexanes:ethyl acetate to give a light yellow foam. The isomers were resolved to give a pure sample of tert-butyl 2-(4-(5-(4-chlorophenylcarbamoyl)-1H-benzo[d]imidazol-1-yl)-3-cyanophenyl)acetate.

Step C: To a mixture of tert-butyl 2-(4-(5-(4-chlorophenylcarbamoyl)-1H-benzo[a]imidazol-1yl)-3cyanophenyl)acetate (0.015 g, 0.029 mmol) in 1 mL DCM was added 0.25 ml of trifloroacetic acid. The reaction mixture was stirred for 3 hours, then concentrated to give an oil. The oil was dissolved in DCM and concentrated under high vacuum to provide 2-(4-(5-(4-chlorophenylcarbamoyl)-1H-benzo[d]imidazol-1-yl)-3-cyanophenyl)acetic acid as the TFA salt (0.015 g, 90%) as a tan solid. ¹H NMR (400 MHz, D6-DMSO) δ 8.75 (s, 1H), 8.63 (t, J=5.8 Hz, NH), 8.31 (s, 1H), 8.08 (s, 1H), 7.81-7.91 (m, 3H), 7.46 (d, J=8.5 Hz, 1H), 7.35 (d, J=7.6 Hz, Step A: A suspension of 2-methyl-1H-benzo[d]imidazole-5carboxylic acid (0.750 g, 4.26 mmol), 2-(4-chlorophenyl)ethanamine (0.596 g, 3.83 mmol), HBTU (1.78 g, 4.68 mmol) and DIEA (1.11 mL, 6.39 mmol) in 10 mL of DCM was stirred at ambient temperature overnight. To the reaction was added DMF (10 mL) which caused a clear solution to form. The reaction was loaded onto a silica gel samplet and the product eluted using a gradient of 0.5% MeOH/DCM to 10% MeOH/DCM. Isolated N-(4-chlorophenethyl)-2-methyl-1H-benzo[d]imidazole-5carboxamide (0.65 g, 48.7% yield) as a yellow oil. MS(ESI)=314.4 (M+1).

Step B: A mixture of tert-butyl 2-(3-cyano-4fluorophenyl) acetate (0.0825 g, 0.351 mmol), N-(4-chlorophenethyl)-2-methyl-1H-benzo[d]imidazole-5carboxamide (0.100 g, 0.319 mmol) and potassium carbonate (0.0661 g, 0.478 mmol) was stirred together in 3 mL of DMSO at 85° C. After stirring for 4 hours, the reaction was loaded onto a silica gel samplet and the product eluted using a gradient of 5% ethyl acetate/hexanes to 100% ethyl acetate/hexanes. The resulting oil was dissolved in DCM (1 mL) and treated with TFA (1 mL). After 2 hours, the reaction was concentrated, and the residue was loaded onto silica gel. The product was eluted using a gradient of 0.5% MeOH/DCM containing 0.5% AcOH to 10% MeOH/DCM containing 0.5% AcOH to provide 2-(4-(5-(4-chlorophenethylcarbamoyl)-2-methyl-1H-benzo[d]imidazol-1yl)3-cyanophenyl)acetic acid and 2-(4-(6-(4-chlorophenethylcarbamoyl)-2-methyl-1H-benzo[d]imidazol-1-yl)-3-cyanophenyl)acetic acid (0.045 g, 29.9% yield) as a 2:1 mixture. $^1$H NMR (400 MHz, CD$_3$OD) δ 8.49 (t, J=5.5 Hz, NH), 7.77-7.82 (m, 2H), 7.68 (s, 1H), 7.52-7.54 (m, 1H), 7.20-7.32 (m, 4H) 7.00-7.08 (m, 2H), 3.71 (s, 2H), 3.58 (q, J=6.8 Hz, 2H), 3.30 (s, 3H), 2.90 (t, J=7.3 Hz, 2H). MS(APCI)=473.5 (M+1).

Example 16

2-(4-(5-((4-Chlorophenethylcarbamoyl)-1H-indazol-1-yl)3-cyanophenyl)acetic Acid

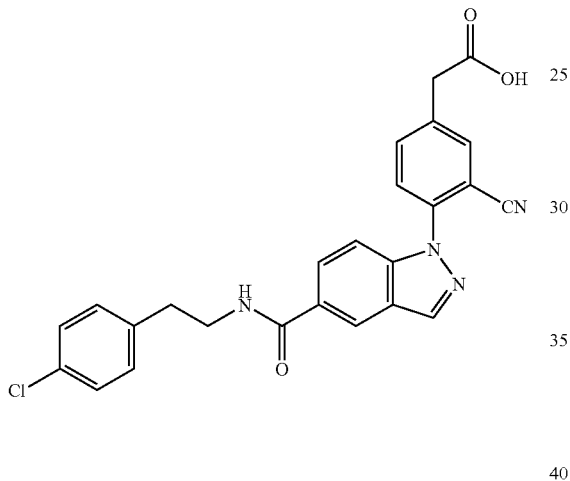

Step A: To a stirred solution of the 1H-indazole-5carboxylic acid (215 mg, 1.32 mmol) and HBTU (553 mg, 1.45 mmol) in DMF (5 mL) was added DIEA (277 μL, 1.59 mmol) followed by 2-(4chlorophenyl)ethylamine (222 μL, 1.59 mmol). The reaction was stirred overnight, then diluted with water and extracted with EtOAc. The combined organic layers were washed with brine and dried over MgSO$_4$. The crude product was purified over silica gel on a Biotage Horizon high-performance flash chromatography system (25+M silica gel cartridge) eluting with a gradient of 0.5% MeOH/DCM to 10% MeOH/DCM to give N-(4-chlorophenethyl)-1H-indazole-5-carboxamide (0.165 g, 42%).

Step B: To a stirred solution of tert-butyl 2-(3-cyano-4-fluorophenyl)acetate (110 mg, 0.468 mmol) and N-(4-chlorophenethyl)-1H-indazole-5-carboxamide (168 mg, 0.561 mmol) in DMSO (2 ml) was added K$_2$CO$_3$ (77.5 mg, 0.561 mmol). The reaction was heated to 90° C. overnight via an oil bath. The reaction was diluted with EtOAc and 10% aqueous sodium carbonate. The aqueous phase was extracted with EtOAc and the combined organic layers were washed with brine, dried over MgSO$_4$, and concentrated. The crude product was purified over silica gel on a Biotage Horizon high-performance FLASH chromatography system (25+M silica gel cartridge) eluting with a gradient of 5% ethyl acetate/hexanes to 70% ethyl acetate/hexanes to provide tert-butyl 2-(4-(5-((4-chlorophenethyl)carbamoyl)-1H-indazol-1-yl)-3-cyanophenyl)acetate (0.241 g, 0.103 mmol, 22%).

Step C: To a fitted solution of tert-butyl 2-(4-(5-((4-chlorophenethyl)carbamoyl)-1H-indazol-1-yl)-3-cyanophenyl) acetate (43.4 mg, 0.084 mmol) in DCM (2 mL) was added TFA (250 μL). The reaction was stirred at ambient temperature for 4 hours and then concentrated. The crude product was purified over silica gel on a Biotage Horizon high-performance FLASH chromatography system (12+M silica gel cartridge) eluting with a gradient of 0.5% MeOH/DCM containing 0.5% AcOH to 5% MeOH/DCM containing 0.5% AcOH to give 2-(4-(5-((4-chlorophenethyl)carbamoyl)-1H-indazol-1yl)-3-cyanophenyl)acetic acid (0.038 g, 0.667 mmol, 79%). $^1$H NMR (400 MHz, CDOD$_3$) δ 8.68 (t, J=5.5 Hz, NH), 8.62 (s, 1H), 8.43 (s, 1H), 8.03 (s, 1H), 7.97 (d J=8.6 Hz, 1H), 7.84 (s, 2H), 7.65 (d, J=8.3 Hz, 1H), 7.35 (d, J=8.4 Hz, 2H), 7.29 (d, J=8.7 Hz, 2H), 3.82 (s, 2H), 3.53 (q. J=6.5 Hz, 2H), 2.88 (t, J=7.3 Hz, 2H). MS(APCI)=459.2 (M+1).

Example 17

2-(4-(5-(1,(2,4-dichlorophenylcarbamoyl)-1H-indol-1-yl)-phenyl)acetic Acid

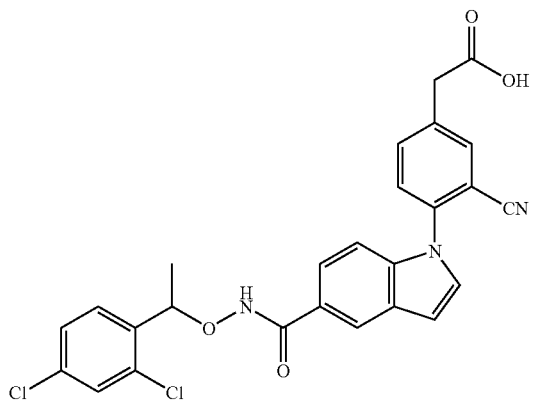 [SMILES: CC(ONC(=O)c1ccc2c(ccn2-c2ccc(CC(=O)O)cc2C#N)c1)c1ccc(Cl)cc1Cl]

Step A: To a solution of 2-hydroxyisoindoline-1,3-dione (1.00 g, 6.13 mmol), triphenylphosphine (1.61 g, 6.13 mmol), and 1-(2,4-dichlorophenyl)ethanol (1.17 g, 6.13 mmol) in 15 mL of tetrahydrofuran at ambient temperature was added dropwise diisopropyl azodicarboxylate (1.24 mmol, 6.13 mmol). After stirring at ambient temperature for 16 hours, the reaction was loaded onto a silica gel samplet and the product was eluted using a gradient of 5% ethyl acetate/hexanes to 50% ethyl acetate hexanes. Isolated 2-(1-(2,4-dichlorophenyl)ethoxy)isoindoline-1,3-dione (1.78 g, 5.29 mmol).

Step B: A mixture of 2-(1-(2,4-dichlorophenyl)ethoxy)-isoindoline-1,3-dione (1.78 g, 5.29 mmol) and hydrazine (0.52 g, 15.97 mmol) in ethanol (12 mL) was stirred at ambient temperature. Isolate O-(1-2,4-dichlorophenyl)ethyl)hydroxylamine.

Step C: 2-(3Cyano-4-(5-(1,(2,4-dichlorophenyl)ethoxycarbamoyl)-1H-indol-1-yl)phenyl)acetic acid was prepared by the method of Example 5, substituting 2-(2,4-dichlorophenyl)ethanamine in Step E with O-(1-(2,4-dichlorophenyl)

ethyl)hydroxylamine. $^1$H NMR (400 MHz, CD$_3$OD) δ 8.02 (s, 1H), 7.90(s, 1H), 7.80(d, J=8.4 Hz, 1H), 7.75 (d, J=7.9 Hz, 1H), 7.61 (d, J=8.5 Hz, 1H), 7.56 (d, J=4.0 Hz, 1H), 7.54 (dd, J=1.6, 8.6Hz, 1H), 7.46 (s, 1H), 7.42 (d, 8.7 Hz, 1H), 7.30 (d, J=8.7 Hz, 1H), 6.82 (d, J=3.2 Hz, 1H), 5.62 (q, J=6.5 Hz, 1H), 3.81 (s, 2H), 1.58 (d, J=6.1 Hz, 3H). MS(APCI)=507.7 (M+1).

What is claimed is:

1. A compound of general Formula I:

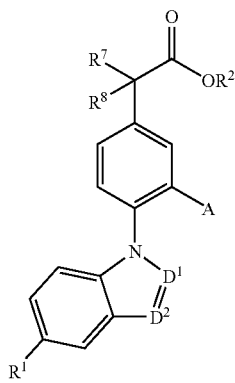

or a salt thereof, wherein:
- $D^1$ is N or $CR^9$ and $D^2$ is N or $CR^{10}$, wherein at least one of $D^1$ and $D^2$ is not N;
- $R^1$ is $Ar^1$ -$L^1$ -W-$L^2$-;
- $L^2$ is —$(CR^cR^d)_m$-;
- W is —$CONR^{3a}$—, —$NR^{3b}CO$— or —$SO_2NR^{3c}$—;
- $R^{3a}$, $R^{3b}$ and $R^{3c}$ are each H or methyl;
- $L^1$ is —$(CR^aR^b)_n$— or —$(CR^aR^b)O$—;
- n and m are independently 0, 1 or 2;
- each $R^a$, $R^b$, $R^c$ and $R^d$ is independently H, F, methyl or cyclopropyl,
- or $R^a$ and $R^b$ or $R^c$ and $R^d$ together with the carbon to which they are attached form a cyclopropyl ring;
- $Ar^1$ is phenyl, naphthyl, or 2,3-dihydro-1H-indenyl, each of which is unsubstituted or substituted with one or more groups independently selected from F, Cl, CN, $CF_3$, $CHF_2$, $CH_2F$, $SF_5$, methyl, ethyl and cyclopropyl, provided that when $Ar^1$ is naphthyl or 2,3-dihydro-1H-indenyl then n is 0;
- $R^2$ is H or $C_1$-$C_6$ alkyl;
- A is CN, $CH_2NH_2$, $CH_2NR^{4a}C(=O)R^5$, $CH_2NR^{4b}SO_2R^6$, or Cl;
- $R^{4a}$ and $R^{4b}$ are each H or methyl;
- $R^5$ is $C_1$-$C_6$ alkyl, $C_1$-$C_6$ alkoxy, or $C_3$-$C_6$ cycloalkyl;
- $R^6$ is $C_1$-$C_6$ alkyl, NH($C_1$-$C_6$ alkyl), or N($C_1$-$C_6$ alkyl)$_2$;
- $R^7$ and $R^8$ are independently H or methyl; and
- $R^9$ and $R^{10}$ are independently H, methyl, ethyl, isopropyl, $CF_3$, or cyclopropyl.

2. A compound as claimed in claim 1, wherein $D^1$ is $CR^9$ and $D^2$ is $CR^{10}$.

3. A compound as claimed in claim 2, wherein $R^9$ and $R^{10}$ are H.

4. A compound as claimed in claim 1, wherein $D^1$ is N and $D^2$ is $CR^{10}$, or $D^1$ is $CR^9$ and $D^2$ is N.

5. A compound as claimed in claim 4, wherein $R^9$ is H and $R^{10}$ is H or methyl.

6. A compound as claimed in claim 1, wherein -$L^1$-W-$L^2$- is selected from —CONH—, —$CH_2$CONH—, —$CH_2CH_2$CONH—, —CONHCH$_2$—, —$CH_2$CONHCH$_2$—, —NHCO—, —$CH_2$NHCO—, —NHCOCH$_2$—, —$CH_2CH_2$NHCO—, —$CH_2$NHCOCH$_2$—, —$CH_2CH_2$NHCOCH$_2$—, —$CH_2$N(CH$_3$)COCH$_2$—, cyclopropylideneCH$_2$NHCO—, —$CH_2$ONHCO—, —$SO_2$NH—, —$CH_2$CH(CH$_3$)NHCO—, —$CH_2$C(CH$_3$)$_2$NHCO— and —CH(CH$_3$)ONHCO—.

7. A compound as claimed in claim 6, wherein -$L^1$-W-$L^2$- is selected from $CH_2CH_2$NHCO—, —CONH—, —$CH_2$CH(CH$_3$)NHCO—, $CH_2$C(CH$_3$)$_2$NHCO—, —NHCO—, —$CH_2$ONHCO—and —$SO_2$NH—.

8. A compound as claimed in claim 1, wherein $Ar^1$ is a naphthyl or phenyl, each of which is unsubstituted or substituted by one or two substituents selected independently from F, Cl and $CF_3$.

9. A compound as claimed in claim 8, wherein $Ar^1$ is naphthyl, phenyl, 4-fluorophenyl, 3,4-difluorophenyl, 2-chlorophenyl, 3-chlorophenyl, 4-chlorophenyl, 3,4-dichlorophenyl, 4-chloro-3-fluorophenyl, 3-chloro-4-fluorophenyl, 4-trifluoromethylphenyl, 3-fluoro-4-trifluoromethylphenyl or 2,4-dichlorophenyl.

10. A compound as claimed in claim 1, wherein $Ar^1$ is 2,3-dihydro-1H-indenyl.

11. A compound as claimed in claim 1, wherein $R^6$ is $C_1$-$C_6$ alkyl.

12. A compound as claimed in claim 1, in which A is selected from CN, Cl and $CH_2NHSO_2CH_3$.

13. A compound as claimed in claim 1, in which A is CN.

14. A compound as claimed in claim 1, in which $R^2$ is hydrogen.

15. A compound as claimed in claim 1, in which $R^7$ and $R^8$ are hydrogen.

16. A pharmaceutical composition comprising a compound of Formula I as defined in claim 1, or a pharmaceutically acceptable salt thereof, and a pharmaceutically acceptable diluent or carrier.

17. A compound of Formula I as defined in claim 1, or a pharmaceutically acceptable salt thereof, for use in therapy.

18. A process for the preparation a compound of claim 1, which comprises:

(a) for a compound of Formula I in which A is CN, reacting a corresponding compound having the formula:

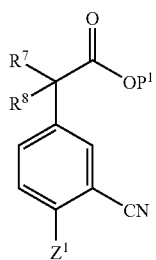

in which $R^7$ and $R^8$ are as defined herein, $P^1$ represents a hydrogen atom or a carboxyl protecting group, and $Z^1$ represents a leaving atom or group, with a compound having the formula

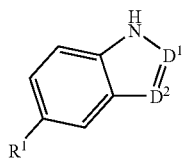

(III)

wherein $D^1$, $D^2$ and $R^1$ are as defined herein, in the presence of a base; or (b) for a compound of Formula I in which A is —CH$_2$NH$_2$, reducing a corresponding compound formula (IV)

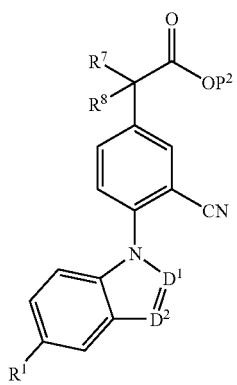

(IV)

in which $D^1$, $D^2$, $R^1$, $R^7$ and $R^8$ are as defined herein and $P^2$ is as defined for $P^1$; or (c) for a compound of Formula I in which A is CH$_2$NR$^{4a}$C(=O)R$^5$ or CH$_2$NR$^{4b}$SO$_2$R$^6$, reacting a corresponding compound of formula (VI)

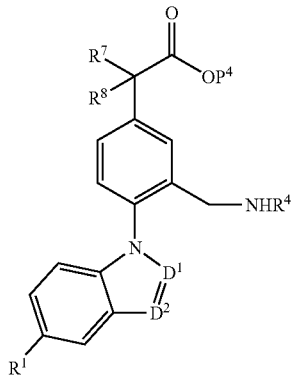

(VI)

in which $D^1$, $D^2$, $R^1$, $R^7$ and $R^8$ are as defined herein, $R^4$ is as defined for $R^{4a}$ and $R^{4b}$, and $P^4$ is as defined for $P^1$, with a compound of formula R$^5$COZ$^2$ or R$^6$SO$_2$Z$^3$ in which Z$^2$ and Z$^3$ each represents a leaving atom or group and R$^5$ and R$^6$ are as defined herein; or (d) coupling a corresponding compound of formula (VII)

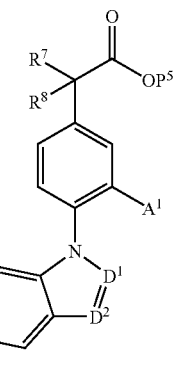

(VII)

in which $D^1$, $D^2$, $R^7$ and $R^8$ are as defined herein, $P^5$ is as defined for $P^1$, $A^1$ represents A or a protected form thereof and $R^{1a}$ represents H—X$^a$-L$^2$- in which X$^a$ represents HN, OC(=O) or SO$_2$, or a reactive derivative thereof, and L$^2$ is as defined herein, with a compound of formula (VIII)

$$Ar^1-L^1-X^b—H \qquad (VIII)$$

in which $X^b$ represents C(=O)O or NH, or a reactive derivative thereof, and Ar$^1$ and L$^1$ are as defined herein; or (e) for a compound of Formula I in which A is Cl or CN, coupling a corresponding compound having the formula (IX)

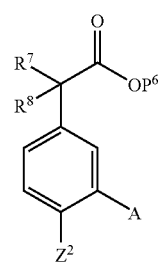

(IX)

in which $R^7$ and $R^8$ are as defined herein, $P^6$ is as defined for $P^1$, and 2 represents a leaving atom or group, with a compound having the formula (X)

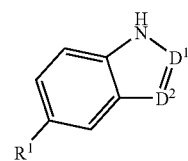

(X)

wherein $D^1$, $D^2$ and $R^1$ are as defined herein, in the presence of an appropriate metal catalyst and base; or (f) for a compound of formula (I) in which A is Cl, and R$^7$ and R$^8$ are each hydrogen, reacting a corresponding compound having the formula (XI):

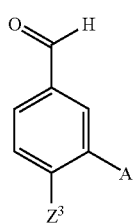
(XI)
in which $Z^1$ represents a leaving atom or group, with a compound having the formula
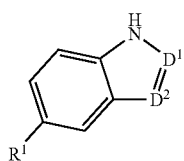
(III)
wherein $D^1$, $D^2$ and $R^1$ are as defined herein, in the presence of a base followed by homologation of the intermediate aldehyde (XII)
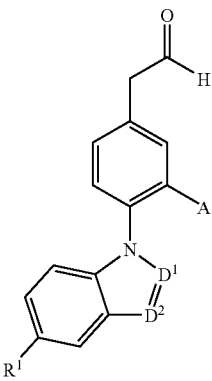
(XII)
to the corresponding carboxylic acid; and
removing any protecting group or groups and, if desired, forming a salt.
\* \* \* \* \*